US009975821B2

(12) United States Patent
Ernst et al.

(10) Patent No.: US 9,975,821 B2
(45) Date of Patent: May 22, 2018

(54) CATALYST BED CONFIGURATION FOR OLEFIN CONVERSION AND PROCESS FOR OBTAINING OLEFINS

(71) Applicant: Borealis AG, Vienna (AT)

(72) Inventors: Eberhard Ernst, Weissenfels (DE); David Linke, Berlin (DE); Mariana Stoyanova, Berlin (DE); Evgeny Kondratenko, Rostock (DE)

(73) Assignee: Borealis AG, Vienna (AT)

( * ) Notice: Subject to any disclaimer, the term of this patent is extended or adjusted under 35 U.S.C. 154(b) by 0 days. days.

(21) Appl. No.: 15/027,451

(22) PCT Filed: Nov. 13, 2014

(86) PCT No.: PCT/EP2014/074438
§ 371 (c)(1),
(2) Date: Apr. 6, 2016

(87) PCT Pub. No.: WO2015/071342
PCT Pub. Date: May 21, 2015

(65) Prior Publication Data
US 2016/0244384 A1    Aug. 25, 2016

(30) Foreign Application Priority Data
Nov. 14, 2013  (EP) .................................. 13192901

(51) Int. Cl.
| | |
|---|---|
| *B01J 8/04* | (2006.01) |
| *B01J 21/10* | (2006.01) |
| *B01J 23/02* | (2006.01) |
| *B01J 23/04* | (2006.01) |
| *B01J 23/28* | (2006.01) |
| *C07C 6/04* | (2006.01) |
| *B01J 37/14* | (2006.01) |
| *B01J 37/18* | (2006.01) |
| *B01J 23/30* | (2006.01) |

(52) U.S. Cl.
CPC ........ *C07C 6/04* (2013.01); *B01J 8/04* (2013.01); *B01J 23/30* (2013.01); *B01J 37/14* (2013.01); *B01J 37/18* (2013.01); *C07C 2521/08* (2013.01); *C07C 2521/10* (2013.01); *C07C 2523/30* (2013.01); *Y02P 20/52* (2015.11)

(58) Field of Classification Search
CPC ..... B01J 8/04; B01J 21/10; B01J 23/02; B01J 23/04; B01J 23/28; B01J 23/30; B01J 37/14; B01J 37/18; C07C 2521/08; C07C 2521/10; C07C 2523/30
USPC ................... 502/251, 254, 305, 306
See application file for complete search history.

(56) References Cited

U.S. PATENT DOCUMENTS

| | | | |
|---|---|---|---|
| 3,365,513 A | 1/1968 | Heckelsberg | |
| 3,546,313 A | 12/1970 | Banks | |
| 3,660,507 A * | 5/1972 | Reusser | .................... C07C 6/04 |
| | | | 585/374 |
| 3,865,751 A | 2/1975 | Banks et al. | |
| 3,915,897 A | 10/1975 | Reusser et al. | |
| 4,547,617 A | 10/1985 | Welch | |
| 4,575,575 A * | 3/1986 | Drake | ..................... B01J 23/30 |
| | | | 585/646 |
| 6,281,402 B1 | 8/2001 | Coupard et al. | |
| 7,223,895 B2 | 5/2007 | Sumner | |
| 7,977,522 B2 | 7/2011 | Takai et al. | |
| 8,586,813 B2 | 11/2013 | Ramachandran et al. | |
| 2010/0056839 A1* | 3/2010 | Ramachandran | ...... B01J 23/007 |
| | | | 585/646 |
| 2010/0167911 A1 | 7/2010 | Shum | |
| 2010/0191030 A1 | 7/2010 | Ikenaga | |
| 2011/0077444 A1* | 3/2011 | Butler | ..................... B01J 21/10 |
| | | | 585/670 |
| 2012/0016172 A1 | 1/2012 | Miyazoe et al. | |
| 2016/0167003 A1* | 6/2016 | Ernst | ........................ C07C 6/04 |
| | | | 585/644 |
| 2016/0229769 A1* | 8/2016 | Ernst | ........................ B01J 8/04 |
| 2016/0318830 A1* | 11/2016 | Stoyanova | ............ C07C 7/1485 |
| 2016/0347687 A1* | 12/2016 | Stoyanova | ............ C07C 5/2512 |

FOREIGN PATENT DOCUMENTS

| | | |
|---|---|---|
| EP | 1854776 A1 | 11/2007 |
| EP | 2184106 A1 | 5/2010 |
| EP | 2415739 A1 | 2/2012 |
| WO | 2005049534 A1 | 6/2005 |
| WO | 2011011173 A2 | 1/2011 |

OTHER PUBLICATIONS

Banks R, et al., New developments and concepts in enhancing activities of heterogeneous metathesis catalysts, Journal of Molecular Catalysis, vol. 28, 1985, pp. 117-131, Abstract included.

* cited by examiner

*Primary Examiner* — Patricia L. Hailey
(74) *Attorney, Agent, or Firm* — The Webb Law Firm

(57) ABSTRACT

The present invention relates to a catalyst bed configuration for conversion of olefins comprising i) at least one main catalyst bed comprising a) at least one first catalyst component comprising a metathesis catalyst, and b) at least one second catalyst component comprising a catalyst for double bond isomerization, and ii) at least one catalyst pre-bed arranged upstream of the at least one main catalyst bed comprising at least one compound selected from the group of alkaline earth oxides. The at least one compound used as catalyst pre-bed and selected from the group of alkaline earth oxides is subjected to a pre-treatment before arranging said at least one compound used as catalyst pre-bed upstream of the at least one main catalyst bed, wherein the pre-treatment comprises at least one cycle comprising successive treatment in an oxidizing and reducing atmosphere.

21 Claims, No Drawings

CATALYST BED CONFIGURATION FOR OLEFIN CONVERSION AND PROCESS FOR OBTAINING OLEFINS

CROSS-REFERENCE TO RELATED APPLICATIONS

This application is the United States national phase of International Application No. PCT/EP2014/074438 filed Nov. 13, 2014, and claims priority to European Patent Application No. 13192901.0 filed Nov. 14, 2013, the disclosures of which are hereby incorporated in their entirety by reference.

BACKGROUND OF THE INVENTION

Field of the Invention

The present invention relates to a catalyst bed configuration, and a process for obtaining an olefin.

Description of Related Art

Butenes are the $C_4H_8$ mono-olefin isomers such as 1-butene, cis-2-butene, trans-2-butene and iso-butene (2-methylpropene). If it is not specifically mentioned, cis-2-butene, trans-2-butene are also called as 2-butene within the frame of the present invention. The sum of cis-2-butene, trans-2-butene, and 1-butene is denoted as n-butenes. Butenes are almost always commercially produced as by-products in a petroleum refinery by cracking processes or by catalytic ethene dimerisation. Butenes can be used for multiple purposes like in the manufacture of polymers and other chemicals like insecticides, antioxidants, adhesives, sealants or elastomers.

The use of n-butenes for the production of propene has gained industrial importance in the last decades. The synthesis of propene using n-butenes as starting material is based on the metathesis reaction. Hereby, 2-butene is converted in the presence of ethene to propene according to the following overall reaction scheme:

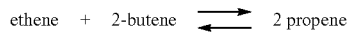

ethene + 2-butene ⇌ 2 propene

This reaction occurs typically in the presence of a catalyst comprising metal oxide of the group 6 or 7 of the periodic system of the elements (PSE). Typical active components of catalysts used for olefin metathesis are tungsten oxide supported on silica (U.S. Pat. No. 3,365,513) or rhenium oxides and molybdenum oxides supported on alumina or silica alumina (U.S. Pat. No. 4,547,617; U.S. Pat. No. 6,281,402).

Various modifications and improvements of the metathesis catalysts have been described. The physical mixing of the metathesis catalyst with an isomerisation catalyst for shifting the double bond in 1-butene to 2-butene has been proven to increase the overall production yield (U.S. Pat. No. 3,865,751; U.S. Pat. No. 3,915,897; U.S. Pat. No. 4,575,575). Typical double bond isomerisation catalysts include basic metal oxides as for instance magnesium oxide or calcium oxide, which can be admixed with the metathesis catalyst. The use of magnesium oxide (MgO) as a co-catalyst enables reduction of the reaction temperature to 250-300° C. from approximately 400° C. for pure silica supported tungsten oxide ($WO_3/SiO_2$). The weight ratio of MgO to $WO_3/SiO_2$ is in the range of 0.1-20. Magnesium oxide has the function to isomerise 1-butene to 2-butene since both olefins are present in technical feeds. It is important to highlight that magnesium oxide alone shows negligible metathesis activity.

Besides its ability to act as an isomerisation catalyst magnesium oxide has also been known for its ability to remove or destroy traces of contaminants from the olefin feed that are detrimental to metathesis catalysts, in particular when used as a "guard bed" (J. Mol. Cat. 1985, 28:117-131). Magnesium oxide can be for instance arranged on top of a composition comprising the metathesis catalyst and an isomerisation catalyst (US 2010/0056839 A1). Here the optimal catalyst activation is combined with the guard pre-bed function to remove poisons and the isomerisation of 1-butene to 2-butene. When applying this approach a technical metathesis reactor is typically filled with a mixture of MgO and $WO_3/SiO_2$ as main bed and an MgO pre-bed upstream of the main bed.

According to US 2010/167911 A1 the catalyst mixture of isomerisation catalyst and metathesis catalyst may be loaded in form of layers in the reactor. Here the catalyst bed may be configured such that the upstream end of the bed is substantially pure isomerisation catalyst and the downstream end of the bed is a mixture of isomerisation catalyst and metathesis catalyst. This whole catalyst mixture may be activated before being introduced to the reactor.

However, the known technical metathesis catalysts for propene production suffer from a decrease in their activity due to coke formation. Therefore, a regeneration of the catalyst is imperative if the catalytic activity decreases below a certain level during the production cycle.

One regeneration method is described for instance in US 2010/0167911 A1 mentioned above. Here an already used catalyst mixture (which has been exposed to olefins before) is regenerated by decoking the used catalyst mixture in the presence of an oxygen containing gas followed by contacting the decoked catalyst mixture with steam at a temperature in the range of 100 to 300° C.

The decoking step is usually performed at temperatures between 450° C. to 800° C. Such high-temperature treatment additionally diminishes the lifetime both of the metathesis catalyst and in particular the isomerisation catalyst.

In WO 2011/011173 A1 it is reported that the performance of MgO as isomerisation catalyst after several regeneration/reaction cycles is low. The reduced performance of the catalyst may lead to a rapid build-up of 1-butene in the system over time thus limiting the overall reactor performance. It is thought that the loss of activity as a result of multiple cycles of regeneration is due to the loss of surface area of the catalyst particle due to sintering created by the higher temperatures required for coke removal. The loss of surface area results in loss of MgO activity for isomerisation and as adsorbent for poisons.

It is therefore highly desirable to provide a catalyst system which is still active also after several cycles of reaction and regeneration in order to improve the catalyst lifetime and allows for an improved overall reactor performance.

SUMMARY OF THE INVENTION

Accordingly, a (whole) catalyst bed configuration for conversion of olefins is provided which comprises
  i) at least one main catalyst bed comprising a) at least one first catalyst component comprising a metathesis catalyst, and b) at least one second catalyst component comprising a catalyst for double bond isomerisation, and ii) at least one catalyst pre-bed arranged upstream of the at least one main catalyst bed comprising at least one compound selected from the group of alkaline earth oxides. Said catalyst pre-bed is in particular located immediately upstream and/or directly on the top layer of the main catalyst bed.

The catalyst bed configuration according to the invention is characterized in that the at least one compound used as catalyst pre-bed and selected from the group of alkaline earth oxides is subjected to a pre-treatment before arranging said at least one compound used as catalyst pre-bed upstream of the at least one main catalyst bed, wherein the pre-treatment comprises at least one cycle of successive treatment in an oxidizing atmosphere and reducing atmosphere. Thus, the catalyst pre-bed compound undergoes a pre-treatment, such as a thermal pre-treatment under specific conditions, before it is even arranged as pre-bed upstream of the main catalyst bed; the pre-treatment of the pre-bed compound takes place separate from any further activation process of the main catalyst bed and its use.

In a preferred embodiment the pre-treatment is preferably carried out in the absence of non-saturated hydrocarbons like olefins. Furthermore, the at least one pre-treatment cycle in an oxidizing and successive reducing atmosphere is preferably carried out at temperatures between 300° C. and 800° C., in particular between 300° C. and 600° C.

Thus, the compound of the pre-bed is subjected to conditions usually applied for activating and regenerating the catalyst mixture without exposure to a non-saturated hydrocarbon feed, such as olefin feed. This is in particular surprising since one would assume that such a thermal pre-treatment (what also could be described as a pre-aging) would rather decrease the pre-bed catalyst activity. In contrast the special pre-treatment of the pre-bed compound such as magnesium oxide can significantly improve the long-term performance of the whole catalyst. If the pre-bed compound is pre-treated over repeated regeneration cycles with oxygen and hydrogen without contacting non-saturated hydrocarbons the long-term catalyst activity is clearly improved. The positive effect of a thermal pre-treatment of a pre-bed compound on the overall catalyst activity has not been described before.

In an embodiment of the present catalyst bed configuration the pre-treatment of the compound used as catalyst pre-bed comprises the steps: a) heating the compound in an inert gas atmosphere to a temperature between 300° C. and 500° C.; b) treating the compound in an oxygen containing atmosphere at temperatures between 400° C. and 600° C.; c) treating the compound in a hydrogen containing atmosphere at temperatures between 300° C. and 500° C.; d) flushing the compound with an inert gas at temperatures between 400° C. and 600° C.; and e) subsequent cooling down the compound.

In a further embodiment the pre-treatment of the compound used as catalyst pre-bed comprises the steps: a) heating the compound in an inert gas atmosphere to 400° C.; b) treating the compound in an oxygen containing atmosphere at temperatures between 500° C. and 550° C., preferably 525° C.; c) treating the compound in a hydrogen containing atmosphere at 400° C., d) flushing the compound with an inert gas at temperatures between 400° C. and 550° C., preferably at 550° C.; and e) subsequent cooling down the compound to a temperature between 200 and 350° C., preferably to 300° C.

In yet a further embodiment the pre-treatment of the compound used as catalyst pre-bed comprises the steps: a) heating the compound in an inert gas atmosphere to 400° C. for example with a heating rate between 3 and 8 K/min, preferably 5 K/min; b) replacing the inert gas atmosphere by an oxygen containing gas atmosphere and simultaneous temperature increase to 500° C. to 550° C., preferably to 525° C., for example with a heating rate between 3 and 8 K/min, preferably 5 K/min, and treating the compound in said oxygen containing flow; b1) cooling the compound to 400° C. for example with a cooling rate of 1 to 4 K/min, preferably 2 K/min, in an inert gas atmosphere; c) treating the compound in a hydrogen containing gas atmosphere at 400° C., d) flushing the compound with an inert gas and increasing the temperature simultaneously to 500° C. to 600° C., preferably to 550° C., for example with a heating rate between 3 and 8 K/min, preferably 5 K/min; and e) subsequent cooling down the compound to a temperature between 200 and 350° C., preferably to 300° C.

In yet another variant the pre-treatment of the compound used as catalyst pre-bed comprises the steps: a) heating the compound in an inert gas atmosphere to 400° C. for example with a heating rate of 5 K/min and keeping the temperature constant for 1 to 3 h, preferably 2 h; b) replacing the inert gas atmosphere by an oxygen containing gas atmosphere and simultaneous temperature increase to 525° C., for example with a heating rate of 5 K/min, and treating the compound in said oxygen containing atmosphere for 1 to 3 h, preferably 2 h; b1) cooling the compound to 400° C. for example with a cooling rate of 2 K/min in an inert gas atmosphere and keeping the temperature constant for 0.25 h to 1 h, preferably for 0.5 h; c) treating the compound in a hydrogen containing gas atmosphere at 400° C. for 0.25 h to 1 h, preferably for 0.5 h, d) flushing the compound with an inert gas and increasing simultaneously the temperature to 550° C. for example with a heating rate of 5 K/min; d1) keeping the temperature constant at 550° C. for 12 to 24 h, preferably for 16 h; and e) subsequent cooling down the compound to 300° C.

It is to be understood that in particular the heating and/or cooling rates as provided above depend on the overall size of the catalyst bed and the reactor size. In particular said heating and/or cooling rates have to be adapted, accordingly. For instance, in case of an upscaling of the reactor size reduced heating rates may be practically in order to ensure a homogenous temperature increase throughout the catalyst bed.

It is preferred, if the above described pre-treatment cycle is carried out once. However, the pretreatment cycle can be repeated at least twice, preferably at least five times, more preferably at least nine times or more.

The inert gas applied and used during the pretreatment of the pre-bed compound may be selected from a group comprising argon, nitrogen or methane. Nitrogen and methane are in particular suitable.

The air flow used for creating the oxygen containing atmosphere can be for example comprise synthetic air with 20 vol % oxygen and 80 vol % nitrogen.

The hydrogen containing atmosphere applied in the pre-treatment cycle comprises 20 to 50 vol. %, preferably 30 to 40 vol. %, most preferably 30 vol. % hydrogen. The remaining gas volume may be nitrogen or any other inert gas. In a preferred embodiment the hydrogen containing atmosphere comprises a mixture of hydrogen:nitrogen=30:70 (vol/vol). It should be pointed out that in case of up-scaling the partial pressure should be maintained.

It is furthermore desirable if the mass ratio of the catalyst pre-bed (which was subjected to the above pre-treatment cycle) and the main catalyst bed comprising metathesis catalyst and isomerisation catalyst is between is between 1:10 and 3:1, preferably between 1:6 and 2:1, most preferably between 1:4 and 1:2. In a most preferred embodiment the mass ratio of pre-bed to main bed catalyst is 1:1. The mass ratio of catalyst pre-bed and main catalyst bed may be thus for instance 2.5:1, 2:1, 1:1 or 1:2. The specific mass ratio of catalyst pre-bed and main catalyst bed can have an impact on the catalytic performance. For instance, the cycle time and production time may increase with rising ratio of catalyst pre-bed to main catalyst bed. An optimal ratio has been found for instance in a range between 1:2 and 2.5:1.

As mentioned previously the catalyst pre-bed comprising the pre-treated alkaline earth oxide may be arranged upstream of the main catalyst bed. The catalyst pre-bed may be arranged on the top of the surface of the main catalyst bed and is thus in direct physical contact to the main catalyst bed. The catalyst pre-bed may also be provided in a first reactor (pre-reactor) which is spatially separated from a second reactor with the main catalyst bed (main synthesis reactor). In this case the first reactor with the pre-treated catalyst pre-bed and the second reactor with the main catalyst bed are arranged sequentially.

The first and second reactors are preferably fixed-bed reactors. Basic types of catalytic fixed-bed reactors are the adiabatic fixed-bed reactor and the isothermal fixed-bed reactor. The adiabatic fixed-bed reactor is preferred for technical processes. Pre-bed and main-bed are usually provided in the fixed-bed reactor in form of random packings of powders, pellets or extrudates, for instance of catalytic pellets.

In an embodiment the at least one first reactor and the at least one second reactor have in each case a length to diameter ratio (l/d ratio) between 1 and 15, preferably between 1 and 10, most preferably between 1 and 5, even more preferably between 1.5 and 3.5.

However, it is also conceivable and possible that the first reactor (pre-bed reactor) and the second reactor (main bed reactor) are of different volumes. It is for instance of an advantage if the first reactor is of a smaller volume than the second reactor. The volume ratio (V/V) of first and second reactors may be 0.05-1.0, preferably 0.1-0.8, more preferably 0.2-0.5, most preferably 0.2-0.3.

It is furthermore preferred if the operational temperature T1 of the first reactor is in a range between 150° C. and 300° C., preferably 200° C. and 300° C., most preferably between 220° C. and 280° C., outmost preferably between 240° C. and 260° C., in particular at 250° C., and the operational temperature T2 of the second reactor is in a range between 250° C. and 350° C., preferably between 270° C. and 330° C., most preferably between 290° C. and 310° C., mostly preferred at 300° C.

In a further embodiment the metathesis catalyst of the main catalyst bed comprises metal oxides from metals of group 6 and 7 of the PSE, in particular tungsten oxide, molybdenum oxide and/or a precursor thereof, which are the active components and are deposited on at least one inorganic carrier. The most preferred metal oxide is tungsten oxide.

Preferably, the at least one inorganic carrier is selected from a group comprising silica, alumina, silica-alumina or aluminium phosphate. The inorganic carrier can contain at least about 0.1 wt % and up to 40 wt % of the active components. Amounts between 1 to 30 wt % are preferred, whereby amounts between 2 to 15 wt % are mostly preferred.

The metathesis catalyst may further comprise at least one oxide of a metal of group I of the PSE or a precursor thereof as for instance comprising oxides, hydroxides, carbonates, bicarbonates, nitrates, acetates of sodium or potassium or mixtures thereof. Especially preferred are the hydroxides of sodium and potassium. Said compounds have the function to modify the surface acidity of the silica in the metathesis catalyst. It is known that the bulk concentration of e.g. sodium in silica has to be lower than 500 ppm (WO 2005/049534). The amount of these modifying compounds can be between 0.01 and 10 wt %, preferably between 0.1 and 1.0 wt % with respect to the metathesis catalyst.

It is further possible that the metathesis catalyst undergoes a pre-treatment with at least one oxide of a metal of group 1 of the PSE or a precursor thereof. For example it is preferred if silica supported tungsten oxide is used as metathesis catalyst it undergoes a pre-treatment with potassium hydroxide.

The BET surface area of the metathesis catalyst is at least >10 m$^2$/g, preferably at least >50 m$^2$/g and mostly preferably at least ≥100 m$^2$/g.

The particle size of the metathesis catalyst depends on the reactor size. When applied as powder like for instance in lab size reactors, the typical particle size of the metathesis catalyst is between 0.3-0.7 mm. When used in larger reactors like for instance technical reactors the particle size is in the range between 1 and 10 mm, preferably between 1 and 8 mm, most preferably between 1 and 5 mm.

In another preferred embodiment said second catalyst component for double bound isomerisation of the main bed composition comprises group 2 metal oxides, in particular magnesium oxide, calcium oxide, barium oxide or strontium oxide.

The isomerisation catalyst may also be activated for instance by heating in a flow stream of an oxygen-containing gas for about 1 to 30 hours at about 250° C. to 800° C. After calcination the isomerisation catalyst may be treated under reducing conditions as for instance with a reducing gas as hydrogen or carbon monoxide (U.S. Pat. No. 4,575,575; U.S. Pat. No. 3,546,313).

Thus, in a further embodiment of the present catalyst bed configuration pre-aged isomerisation catalyst such as pre-aged MgO can be used in the main catalyst bed as isomerisation catalyst while a pre-aged alkaline earth oxide e.g. pre-aged or pre-treated MgO is used simultaneously as catalyst pre-bed. The isomerisation catalyst of the main catalyst bed and the alkaline earth oxide of the catalyst pre-bed were preferably pre-treated in the same manner and under the same conditions as described above.

The main catalyst bed can then be prepared by admixture of the isomerisation catalyst and the metathesis catalyst. The catalysts are preferably mixed in form of powders, pellets or extrudates.

The amount of the isomerisation catalyst is preferably in excess of the amount of the metathesis catalyst. However, the isomerisation catalyst can also be used in lower amounts.

In an embodiment the main catalyst bed comprises the at least one isomerisation catalyst component and the at least one metathesis catalyst component in a ratio between 5:1 and 1:1, preferably in a ratio 4:1 and 2:1, most preferably in a ratio of 3:1.

The present catalyst bed configuration comprising the main catalyst bed of metathesis catalyst and isomerisation catalyst and the pre-treated catalyst pre-bed is activated before the actual metathesis reaction of olefins.

Such an activation process may comprises the steps of:
a) heating the catalyst bed in an inert gas atmosphere to a temperature between 300° C. and 500° C., preferably 400° C.;

b) treating the catalyst bed in an oxygen containing atmosphere e.g. such as air at temperatures between 400° C. and 600° C., preferably 400° C. and 550° C.;

c) treating the catalyst bed in a hydrogen containing atmosphere at temperatures between 300° C. and 500° C., preferably at 400° C., d) heating the catalyst bed in an inert gas atmosphere at temperatures between 400° C. and 600° C., preferably 400° C. and 550° C.; and e) subsequent cooling down the catalyst bed in an inert gas atmosphere.

In a typical embodiment of the activation procedure the catalyst bed is heated starting at room temperature for example at a heating rate of 5 K/min until an end temperature e.g. of about 400° C. is reached and is held at this temperature for about 2 hours.

In the next step the catalyst bed is treated in air, wherein the start temperature may be 400° C. and the end temperature may be 525° C. The heating rate is for example about 5 K/min during the oxidation. The holding time at the end temperature may be about 2 hours.

Subsequently the catalyst bed treated in the oxidizing atmosphere is cooled down in an inert gas atmosphere, such as nitrogen gas atmosphere from the oxidation temperature of e.g. 525° C. to 400° C. (for example with a of cooling rate 2 K/min) and is held at the latter temperature for about 0.5 h. The treatment of the catalyst bed under reducing conditions is carried out in a gas mixture of nitrogen and hydrogen with a molar ratio of about 80:20, preferably 70:30 at e.g. about 400° C. for about 0.5-1 h, preferably for about 0.5 h. Following the reduction the catalyst is now purged with nitrogen at 400° C. for about 0.5-1 h, preferably for about 0.5 h.

The catalyst bed treatment under reducing conditions is followed by a heating (desorption) step in an inert gas atmosphere, e.g. nitrogen gas. The desorption step may last 10-20 h, preferably 14-16 h. During this time the temperature may be raised from about 400° C. to about 550° C. for example with a heating rate of about 5 K/min. Finally, the catalyst bed is cooled down in an inert gas atmosphere, e.g. nitrogen gas.

After each metathesis cycle the present catalyst bed configuration undergoes a regeneration cycle.

The regeneration cycle includes heating in an oxygen gas atmosphere at temperatures between 400° C. and 600° C., preferably between 420° C. and 550° C. In a preferred embodiment the catalyst bed configuration is heated at 420° C. in an oxidizing atmosphere with 1-2 vol % oxygen, e.g. 1 vol % oxygen in nitrogen, followed by increasing the oxygen concentration to 3 to 4 vol %, preferably 3 vol % with a simultaneous temperature rise to 480° C. and a further increase of oxygen concentration to 5 to 7 vol % oxygen, preferably 6 vol % oxygen, with a simultaneous temperature rise to 525° C. Subsequently, the catalyst bed configuration is subjected to an air atmosphere at temperatures between 450° C. and 550° C., preferably 525° C., for 1 to 5 h, preferably 3 h, followed by cooling down to a temperature between 300° C. and 400° C., preferably to 400° C., in an inert gas atmosphere, such as nitrogen atmosphere.

In a preferred embodiment the regeneration cycle is followed by an activation cycle before starting the next metathesis cycle. This activation/regeneration/metathesis cycle can be repeated several times, for example at least twice, preferably at least five times, more preferably at least nine times.

The present catalyst bed configuration is preferably used in a reactor and in a process for the conversion of at least two olefins by metathesis. It is in particular preferred if the present catalyst bed configuration is used for the conversion of ethene and at least one butene (e.g. 2-butene) to propene by metathesis.

The catalyst bed configuration is preferably part of a fixed-bed reactor. Basic types of catalytic fixed bed reactors are the adiabatic fixed-bed reactor and the isothermal fixed bed reactor. The adiabatic fixed-bed reactor is preferred for technical processes. The catalyst bed configuration is usually provided in the fixed-bed reactor in form of random packings of powders, pellets or extrudates, for instance of catalytic pellets. As mentioned above it is however also possible that the catalyst pre-bed and the main catalyst bed are arranged spatially separated in two different reactors.

Typically the reactor is a packed fixed-bed reactor, which is widely used for gas solid reactions.

In an embodiment the reactor has a length to diameter ratio (l/d ratio) between 1 and 15, preferably between 1 and 10, most preferably between 1 and 5, even more preferably between 1.5 and 3.5.

The catalyst bed configuration and the reactor are used in a process for obtaining an olefin, in particular propene, by metathesis comprising the steps of feeding at least two olefins as starting material to a reactor, in particular a fixed bed reactor, comprising at least one of the present catalyst bed configurations, and converting the at least two olefins at a pressure between 1 to 50 bar, in particular between 10 to 30 bar, at a temperature between 100 and 600° C., in particular between 250 and 500° C. to at least one new olefin by metathesis.

The metathesis reaction is preferably performed at a weight hourly space velocity (WHSV) in the range between 1 and 100 $h^{-1}$, preferably between 1 and 50 $h^{-1}$, more preferably between 1 and 10 $h^{-1}$ (the WHSV values are referring to the main catalyst bed and the fed 2-buten).

In an embodiment the one of the at least two olefins used as starting material comprises at least two carbon atoms, such as ethene, and the second of the at least two olefins used as starting material comprises at least four carbon atoms, such as 2-butene. The mole ratio between said olefin comprising at least two carbon atoms and the olefin comprising at least four carbon atoms can be between 1 and 20, preferably 1 and 10, mostly preferably between 1 and 5.

The at least two olefins may be supplied to the reactor as a mixed stream or in form of separated streams. When using 2-butene as starting material, the butene component may be supplied as cis- or trans-2-butene or mixtures thereof. A technical 2-butene stream may contain additional small amounts of n-butane, isobutane, isobutene, 1-butene. In some embodiments the mixed C4 stream is pre-treated to increase the 2-butene content in the feed for the metathesis reaction. If a crude C4 cut from an e.g. naphtha cracker is used compounds like 1,3-butadiene, allene or acetylenes have to be removed by a selective hydrogenation step.

The olefin mixture is then contacted with the catalyst bed, whereby the olefins contact at first the catalyst pre-bed where a partial isomerisation of 1-butene to 2-butene may occur. When entering the main catalyst bed comprising the metathesis catalyst and the isomerisation catalyst, isomerisation in particular of 1-butene to 2-butene and the synthesis of propene from ethene and 2-butene occur. Besides propene also other reaction products can be formed such as for example C5-C6 olefins.

The process may be carried out by contacting the olefins with the catalysts in the liquid phase or the gas phase depending on structure and molecular weight of the olefins used as starting material, the catalyst used and/or the reaction conditions applied such as pressure, temperatures etc. Diluents such as saturated aliphatic hydrocarbons, such as methane, ethane, propane, butane and/or inert gases like nitrogen or argon might be suitable. In any case, the presence of deactivating substances like water or oxygen should be avoided.

The metathesis catalyst is very sensitive to impurities in the feed stream. Such feed poisons are, for example, strong polar or protic compounds such as N—, O—, S— and halogen comprising compounds or carbon oxide derivatives. Typical examples are water, alcohols, ethers, ketones, aldehydes, acids, carbon dioxide, carbon monoxide, carbon oxide sulfide and the like. The consequences are reduced catalyst activity and shortened cycle times. Therefore the feed stream must be purified by passing it through suitable adsorbents before feeding to the reactor.

It is also possible to conduct the reaction in the presence of hydrogen (EP 1854776 A1).

The effluent from the metathesis reactor can be sent to a separation system for separating the product(s) from unreacted feed components. For instance, the products of the separation system may include ethene, propene, C4- and C5-compounds. The propene separated from the reaction stream is characterised by a high purity. The ethene and C4 olefins may be recycled back to the metathesis reactor or to a pre-treatment stage.

DETAILED DESCRIPTION OF THE INVENTION

The present invention is further explained in more detail by the means of the following examples.

Example 1: Catalyst Preparation and Pre-Aging Procedure

The $WO_x/SiO_2$ catalyst has been prepared according to U.S. Pat. No. 4,575,575 (see example 1, catalyst component C). Commercial MgO has been used.

In order to prove if MgO loses its improving effect on propene production over several metathesis/regeneration cycles, MgO was pre-aged according to the standard procedure of catalyst treatment described below without exposure to olefin feed.

Pre-Treatment (Pre-Aging) Procedure

MgO was initially heated in a continuous flow reactor using a flow of pure nitrogen up to 400° C. with a heating rate of 5 K·min$^{-1}$. The temperature was held constant for 2 h. Hereafter, the nitrogen flow was replaced by an air flow with a simultaneous increase in temperature to 525° C. with a heating rate of 5 K·min$^{-1}$. After 2 hours in this flow at the final temperature, the reactor was cooled to 400° C. (2 K·min$^{-1}$) in a flow of pure nitrogen. The temperature was held constant for 0.5 h followed by feeding an $H_2:N_2=30:70$ (mol/mol) flow for 0.5 h. Then, the reactor was flushed with a flow of pure nitrogen and heated in the same flow up to 550° C. with a heating rate of 5 K·min$^{-1}$. The temperature was held constant for 16 h. Finally, the reactor was cooled down to 300° C. After finishing this cycle the above procedure was additionally repeated for 5 times. Such treated MgO is called pre-aged MgO.

Example 2: Catalytic Testing

Catalytic tests were performed in a reactor system equipped with 16 continuous-flow fixed-bed quartz reactors operating in parallel under identical conditions, i.e. total pressure of 1.4 bar, reaction temperature of 300° C. and a $C_2H_4$:trans-2-$C_4H_8$:$N_2$=64.3:25.7:10 feed. The total gas flow in each reactor was 14.9 ml (STP)·min$^{-1}$ yielding a WHSV (weight hourly space velocity) of 1.9 h$^{-1}$ related to trans-2-$C_4H_8$. One reactor was always empty and used for by-pass measurements. $C_2H_4$ (Linde, purity>99.95%), trans-2-$C_4H_8$ (Linde, purity>99.0%) were extra purified with molsieve 3 A, while "oxysorb" and molsieve 3 A were applied for purifying $N_2$ (Air Liquide, purity>99.999%). The main catalyst bed is a physical mixture of MgO (0.3-0.7 mm) and $WO_x/SiO_2$ (0.3-0.7 mm) with a weight ratio of 3. MgO (0.3-0.7 mm) was additionally used as a pre-bed arranged upstream. Both beds were packed within the isothermal zone of the reactor. The reactor is heated by an electrical furnace, which is located inside a box pre-heated to 120° C. Up- and downstream lines to the reactor are also inside this box.

Example 3: Embodiment According to the Invention 300 mg of main catalyst bed (see example 2) and 300 mg of pre-aged MgO pre-bed (see example 1) arranged upstream the main bed were loaded in a quartz reactor and used over 9 metathesis cycles and 8 regeneration cycles. The reaction conditions are defined in example 2.

Example 4: Comparative Example

For comparative purposes, a metathesis reaction as described in example 3 was performed, however, using freshly prepared MgO instead of the pre-aged one; i.e. 300 mg main catalyst bed (see example 2) and 300 mg of freshly prepared MgO pre-bed.

It should be mentioned that the tests in examples 3 and 4 were simultaneously carried out in the same set-up (see example 2). This means that the differently composed catalysts were analysed under identical conditions. The duration of selected metathesis cycles and selected catalytic performance at the cycle end are given in Table 1.

Activation Procedure

Before each metathesis cycle, the reactor filled with the whole catalyst bed was heated in a flow of pure nitrogen up to 400° C. with a heating rate of 5 K·min$^{-1}$. The temperature was held constant for 2 h. Hereafter, an air flow was fed to the reactor followed by temperature rising to 525° C. with a heating rate of 5 K·min$^{-1}$. After 2 hours in this flow at the final temperature, the reactor was cooled to 400° C. (2 K·min$^{-1}$) in a flow of pure nitrogen. The temperature was held constant for 0.5 h followed by feeding an $H_2:N_2=30:70$ (mol/mol) flow for 0.5 h. Then, the reactor was flushed with a flow of pure nitrogen and heated in the same flow up to 550° C. with a heating rate of 5 K·min$^{-1}$. The temperature was held constant for 16 h. Finally, the reactor was cooled down to 300° C., where the metathesis reaction was started.

Regeneration Procedure

After completing each metathesis cycle the catalyst was heated in an $O_2$ (1 vol. % in $N_2$) flow up to 420° C. followed by increasing $O_2$ concentration to 3 vol. % with a simultaneous rise in reaction temperature to 480° C. Hereafter, these both parameters were again increased to 6 vol. % and 525° C., respectively. Finally, pure air was fed to the reactor at 525° C. for 3 hours followed by cooling down to 400° C. in a nitrogen flow. Then, the above activation procedure was repeated before starting next metathesis cycle. The duration of selected metathesis cycles and selected catalytic performance at the cycle end are given in Table 1.

TABLE 1

Conversion of n-butenes (X(n-butenes)) and propene selectivity (S(C$_3$H$_6$)) at the end of metathesis cycle as described in examples 3 and 4. $n$(C$_3$H$_6$) represents an overall amount of propene formed during each cycle.

| Cycle number | Time on stream/h | X(n-butenes)/ Example 3 | X(n-butenes)/ Example 4 | S(C$_3$H$_6$)/ Example 3 | S(C$_3$H$_6$)/ Example 4 | $n$(C$_3$H$_6$)/mol Example 3 | $n$(C$_3$H$_6$)/mol Example 4 |
|---|---|---|---|---|---|---|---|
| 1 | 186 | 0.72 | 0.51 | 0.996 | 0.996 | 3.17 | 3.03 |
| 2 | 140 | 0.57 | 0.34 | 0.997 | 0.997 | 2.13 | 1.94 |
| 9 | 140 | 0.48 | 0.20 | 0.995 | 0.999 | 2.26 | 2.11 |

It was expected that the pre-aging of the magnesium oxide would negatively influence its on-stream activity. Surprisingly, the results in table 1 clearly demonstrate that a simple oxidative thermal treatment combined with a hydrogen reduction step is beneficial for on-stream propene production. This is valid both for short and long metathesis cycles with the highest being achieved for industrially attractive long time on stream tests.

The invention claimed is:

1. A catalyst system for conversion of olefins comprising at least one main catalyst bed comprising
   a) at least one first catalyst component comprising a metathesis catalyst, and
   b) at least one second catalyst component comprising a catalyst for double bond isomerisation, and
   at least one thermally pre-treated (pre-aged) catalyst pre-bed that is arranged upstream of the at least one main catalyst bed,
   wherein the at least one thermally pre-treated (pre-aged) catalyst pre-bed comprises at least one compound selected from the group of alkaline earth oxides,
   wherein the at least one compound forming the catalyst pre-bed was thermally pre-treated in at least one cycle comprising a successive treatment in an oxidizing and reducing atmosphere carried out at temperatures between 300° C. and 800° C., and
   wherein the at least one compound is arranged after said successive treatment in catalyst pre-bed upstream of the at least one main catalyst bed.

2. The catalyst system according to claim 1, wherein the pre-treatment of the at least one compound of the catalyst pre-bed comprises the steps:
   a) heating the at least one compound in an inert gas atmosphere to a temperature between 300° C. and 500° C.;
   b) treating the at least one compound in an oxygen containing atmosphere at temperatures between 400° C. and 600° C.;
   c) treating the at least one compound in a hydrogen containing atmosphere at temperatures between 300° C. and 500° C.;
   d) flushing the at least one compound with an inert gas at temperatures between 400° C. and 600° C.; and
   e) subsequently cooling down the at least one compound.

3. The catalyst system according to claim 2, wherein the inert gas is selected from a group consisting of argon, nitrogen or methane.

4. The catalyst system according to claim 1, wherein the pre-treatment of the at least one compound of the catalyst pre-bed comprises the steps:
   a) heating the at least one compound in an inert gas atmosphere to 400° C.;
   b) treating the at least one compound in an oxygen containing atmosphere at temperatures between 500° C. and 550° C.;
   c) treating the at least one compound in a hydrogen containing atmosphere at 400° C.,
   d) flushing the at least one compound with an inert gas at temperatures between 400° C. and 550° C.; and
   e) subsequently cooling down the at least one compound to a temperature between 200° C. and 350° C.

5. The catalyst system according to claim 1, wherein the pre-treatment of the at least one compound if the catalyst pre-bed comprises the steps:
   a) heating the at least one compound in an inert gas atmosphere to 400° C.;
   b) replacing the inert gas atmosphere by an oxygen containing gas atmosphere and simultaneous temperature increase to 500° C. to 550° C. and treating the at least one compound in said oxygen containing flow;
   b1) cooling the at least one compound to 400° C., in an inert gas atmosphere;
   c) treating the at least one compound in a hydrogen containing gas atmosphere at 400° C.,
   d) flushing the at least one compound with an inert gas and increasing the temperature simultaneously to 500° C. to 600° C.; and
   e) subsequently cooling down the at least one compound to a temperature between 200° C. and 350° C.

6. The catalyst system according to claim 1, wherein the pre-treatment cycle is repeated at least twice.

7. The catalyst system according to claim 6, wherein the pre-treatment cycle is repeated at least 5 times.

8. The catalyst system according to claim 1, wherein the main catalyst bed comprises the at least isomerisation catalyst component and the at least one metathesis catalyst component in a ratio between 5:1 and 1:1.

9. The catalyst system according to claim 1, wherein the metathesis catalyst comprises oxides of metals of the 6th and 7th group of the PSE deposited on at least one inorganic carrier.

10. The catalyst system according to claim 9, wherein the metathesis catalyst comprises tungsten oxide, molybdenum oxide, and/or a precursor thereof deposited on at least one inorganic carrier.

11. The catalyst system according to claim 1, wherein said second catalyst component for double bound isomerisation of the main catalyst bed comprises Group 2 metal oxides.

12. The catalyst system according to claim 11, wherein said second catalyst component for double bond isomerisation of the main catalyst bed comprises magnesium oxide, calcium oxide, barium oxide, strontium oxide, or mixtures thereof.

13. The catalyst system according to claim 1, wherein the mass ratio of the pre-bed and the catalyst mixture of metathesis catalyst and isomerisation catalyst is between 1:10 and 3:1.

14. The catalyst system according to claim 1, wherein said at least one compound of the catalyst pre-bed comprises an oxide selected from the group consisting of magnesium oxide, calcium oxide, strontium oxide, barium oxide or mixtures thereof.

15. The catalyst system according to claim 1, wherein said at least one compound of the catalyst pre-bed comprises magnesium oxide.

16. The catalyst system according to claim 1, wherein the isomerisation catalyst of the main catalyst bed underwent a pre-treatment.

17. The catalyst system according to claim 16, wherein the isomerisation catalyst of the main catalyst bed underwent the same pre-treatment as the alkaline earth oxide of the catalyst pre-bed.

18. The catalyst system according to claim 1, wherein the at least one main catalyst bed and the at least one catalyst pre-bed comprising the at least one pre-treated compound are activated in a process comprising the steps of
   a) heating the catalyst bed and the catalyst pre-bed in an inert gas atmosphere to a temperature between 300° C. and 500° C.;
   b) treating the catalyst bed and the catalyst pre-bed in an oxygen containing atmosphere at temperatures between 400° C. and 600° C.;
   c) treating the catalyst bed and the catalyst pre-bed in a hydrogen containing atmosphere at temperatures between 300° C. and 500° C.;
   d) heating the catalyst bed and the catalyst pre-bed in an inert gas atmosphere at temperatures between 400° C. and 600° C.; and
   e) subsequently cooling down the catalyst bed and the catalyst pre-bed in an inert gas atmosphere.

19. A process for obtaining an olefin by metathesis comprising the steps of
   feeding at least two olefins as starting material to a reactor comprising a catalyst system according to claim 1; and
   converting the at least two olefin gases at a pressure between 1 to 50 bar at a temperature between 100° C. and 600° C. to at least one new olefin.

20. The process for obtaining an olefin according to claim 19, wherein the reactor is a fixed-bed reactor.

21. The catalyst system according to claim 1, wherein the at least one compound of the catalyst pre-bed was thermally pre-treated at temperatures between 300° C. and 600° C.

* * * * *